United States Patent [19]
Grozinger

[11] Patent Number: 6,111,112
[45] Date of Patent: Aug. 29, 2000

[54] SYNTHESIS OF 3-AMINO-2-CHLORO-4-METHYLPYRIDINE FROM MALONONITRILE AND ACETONE

[75] Inventor: Karl Grozinger, Ridgefield, Conn.

[73] Assignee: Boehringer Ingelheim Pharmaceuticals, Inc., Ridgefield, Conn.

[21] Appl. No.: 09/478,558

[22] Filed: Jan. 6, 2000

Related U.S. Application Data

[60] Provisional application No. 60/116,704, Jan. 22, 1999.

[51] Int. Cl.[7] .................................................. C07D 213/72
[52] U.S. Cl. ............................................................ 546/250
[58] Field of Search .............................................. 546/250

[56] References Cited

U.S. PATENT DOCUMENTS

| | | |
|---|---|---|
| 5,200,522 | 4/1993 | Grozinger et al. . |
| 5,366,972 | 11/1994 | Hargrave et al. . |
| 5,654,429 | 8/1997 | Nummy . |
| 5,668,287 | 9/1997 | Grozinger et al. . |
| 5,686,618 | 11/1997 | Schneider . |

OTHER PUBLICATIONS

Bagley, et al., Synthesis and alpha–2–Adrenergic Activities of Imidazole and Imidazolidine Analogues: In Vitro and In Vivo Selectivity, Med. Chem. Res. 4: 346–364, 1994.
Norman, et al. Structural Elucidation of an Oxazolo[5,4-b] pyridine: an Alternative Cyclization Product Related to Nevirapine, J. Heterocyclic Chem., 30: 771–779, 1993.
Klunder, et al. Novel Non–Nucleoside Inhibitors of HIV–1 Reverse Transcriptase. 2. Tricyclic Pyridobenzoxazepinones and Dibenzoxazepinones, J. Med. Chem., 35, 1887–1897, 1992.
Chapman, et al; J. Chem. Soc. Perkin Trans. I, 2398–2404; 1980.
Grozinger, et al; J. Heterocyclic Chem., 32, 259; 1995.
Zhang, et al; Tetrahedron 51(48), 13177–13184; 1995.
Hargrave, et al; J. Heterocyclic Chem., 34, 223; 1991.

Primary Examiner—Joseph McKane
Assistant Examiner—Sonya N. Wright
Attorney, Agent, or Firm—Robert P. Raymond; Alan R. Stempel; Mary-Ellen M. Devlin

[57] ABSTRACT

A method for making 3-amino-2-chloro-4-methylpyridine from malononitrile, as depicted in the following reaction scheme.

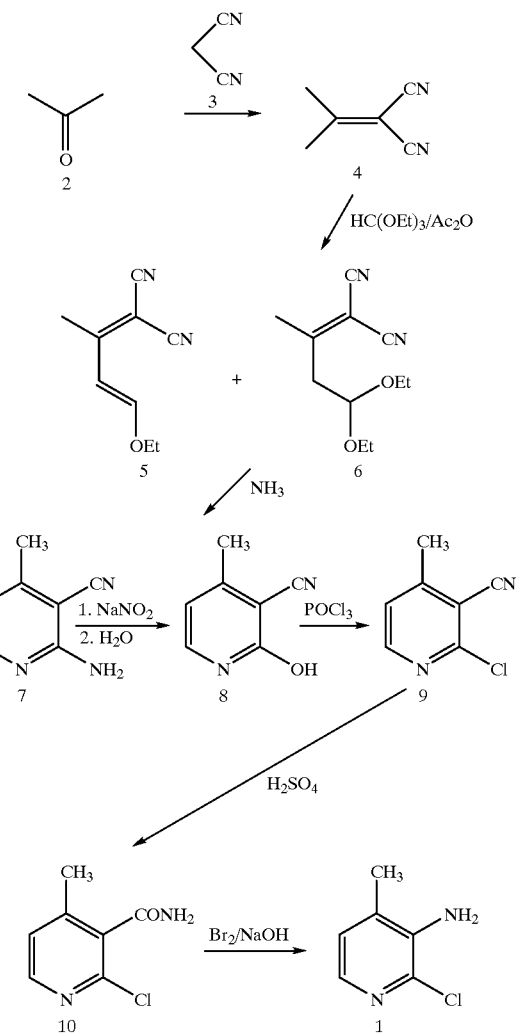

1 Claim, No Drawings

SYNTHESIS OF 3-AMINO-2-CHLORO-4-METHYLPYRIDINE FROM MALONONITRILE AND ACETONE

RELATED APPLICATIONS

The benefit of prior provisional application Ser. No. 60/116,704, filed on Jan. 22, 1999, is hereby claimed.

BACKGROUND OF THE INVENTION

1. Field of the Invention

The present invention relates to a regioselective method for making 3-amino-2-chloro-4-methylpyridine from malononitrile and acetone.

2. Description of Related Art Including Information Disclosed Under 37 CFR 1.97 and 1.98

As described in U.S. Pat. No. 5,366,972, the compound 3-amino-2-chloro-4-methylpyridine is useful as an intermediate material for the synthesis of 11-cyclopropyl-5,11-dihydro-4-methyl-6H-dipyrido[3,2-b:2',3'-e][1,4]diazepin-6-one, an HIV reverse transcriptase inhibitor useful for the treatment of HIV-1, known as nevirapine.

There are several known methods for the synthesis of 3-amino-2-chloro-4-methylpyridine. An early synthesis, beginning from 2-chloro-4-methyl-3-nitropyridine, has been described by Chapman et al. (J. Chem. Soc. Perkin Trans. I, 2398–2404 (1980)). As reported by Grozinger et al. (J. Heterocyclic Chem., 32, 259 (1995)), the compound has been synthesized in small laboratory batches by nitrating the readily available 2-amino-4-picoline or 2-hydroxy-4-picoline. This procedure suffers from non-selective nitration at positions 3 and 5, as well as thermo-chemical hazards and potential for "run-away" when carried out in large. The drawbacks of the nitration-based process lead to the development of two related synthetic routes starting from ethylacetoacetone and cyanacetamide, as described in U.S. Pat. Nos. 5,668,287 and 5,200,522. Both of the latter two synthetic routes require the dichlorination of the intermediate 2,6-dihydroxy-4-methyl-3-pyridinecarbonitrile, at positions 2 and 6, subsequent de-chlorination and finally selective re-chlorination at position 2. The di-chlorination and dehalogenation, as well as the selective monochlorination at position 2 require special manufacturing equipment that is expensive and which may not be readily available. Yet another synthesis, comprising the steps chlorination of ethyl cyanoacetate, Michael addition with crotonaldehyde, cyclization, conversion to the amide and finally reduction to the amine has been described by Zhang et al. (Tetrahedron 51(48), 13177–13184 (1995)), who report that while the desired product was obtained, the Michael addition was slow and the cyclization low-yielding. Schneider (U.S. Pat. No. 5,686,618) has provided a synthesis involving the reduction of 2,6-dichloro-3-amino-4-methylpyridine and monochlorination on position 2 using $H_2O_2$ in HCl, suitable for use on an industrial scale. A synthesis beginning with 2-chloro-3-aminopyridine has been disclosed by Nummy (U.S. Pat. No. 5,654,429).

SUMMARY OF THE INVENTION

The present invention provides an improved method for making 3-amino-2-chloro-4-methylpyridine which comprises the steps depicted below in the following reaction scheme.

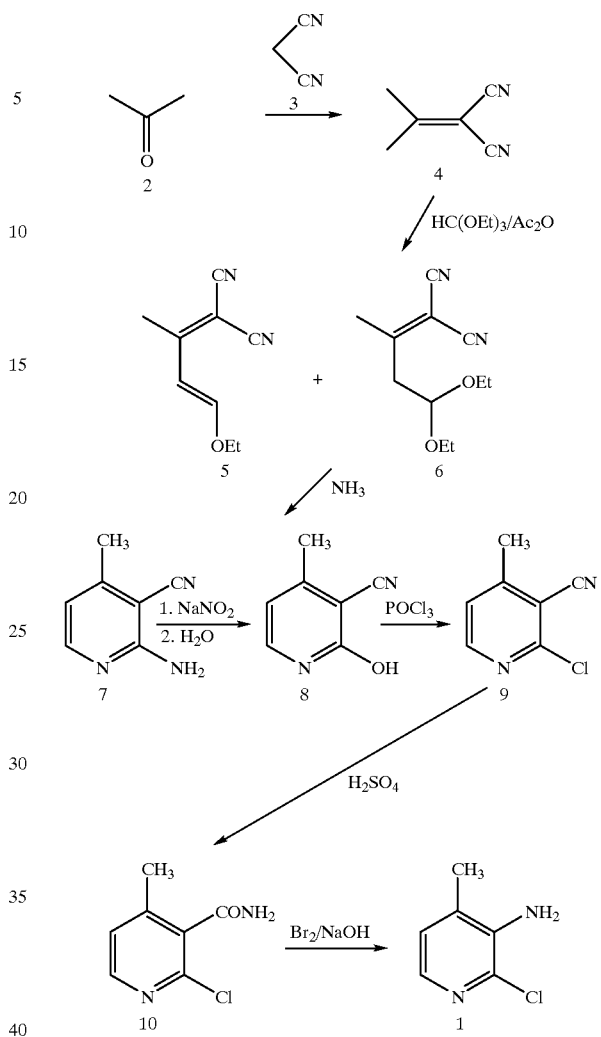

In accordance with the invention, and as shown in the reaction scheme shown above, the Knoevenagel reaction of acetone (2) with malononitrile (3) gives isopropylidenemalononitrile (4). This is condensed with triethyl orthoformate in acetic acid anhydride to give a mixture of the beta-gamma-unsaturated aldehyde equivalent (5) and the enol ether (6). The mixture of (5) and (6) is ring closed with anhydrous ammonia in ethanol, to give 2-amino-4-methyl-pyridine-carbonitrile (7). The intermediate (7) is converted with sodium nitrite to the diazonium salt which is then treated in situ with water to yield the 2-hydroxy-4-methyl-3-cyanopyridine (8). The 2-hydroxy-pyridine derivative (8) is chlorinated with phosphorus oxychloride to yield 2-chloro-4-methyl-3-pyridinecarbonitrile (9). The nitrile (9) is hydrolyzed in concentrated sulfuric acid to yield 2-chloro-4-methyl-3-carboxamide (10). Finally, the amide (10) is converted via the Hofmann amide degradation reaction (treatment with solution of chlorine or bromine in excess sodium hydroxide by means of hypohalides), in a known per se manner, to the desired end product, 3-amino-2-chloro-4-methylpyridine (1).

DESCRIPTION OF THE PREFERRED EMBODIMENT

The following examples describe, in greater detail, the several steps of the process according to the invention and, together, represent the presently preferred embodiment of the invention.

EXAMPLE 1

Synthesis of 2-(1-methylethylidene) malononitrile (4)

Malononitrile (3) was warmed to 50–60° C. until the contents melted. 200 g of the liquefied malononitrile was poured into a 2000 mL three neck round bottom flask containing 600 mL of MTBE (tert-butyl methyl ether) and equipped with a stirrer, reflux condenser and heating mantle. To the mixture was added 232 g of acetone (2), 40 mL of acetic acid and 2 g of beta-alanine. The reaction mixture was heated to reflux using a Dean Stark trap for two days. A total of 55 mL of water was collected. The reaction mixture was cooled and washed two times with 250 mL of water and one time with 250 mL of a saturated sodium chloride solution. The organic layer was dried over anhydrous magnesium sulfate, filtered and concentrated to dryness to yield 283 g of an amber colored oil. The oil was distilled using a vigreux distilling column at 0.05 to 0.02 mm Hg at 56–60° C.

Yield 242.8 g (84% theory) of 4.

EXAMPLE 2

Synthesis of 2-(3-ethoxy-1-methyl-(E)-2-propenylidene)malononitrile (5) and 2-(3.3-diethoxy-1-methylpropylidene)malononitrile (6)

To a 1 liter three neck flask equipped with a reflux condenser and a heating mantle was added 165 g of isopropylidenemalononitrile (4), 280 mL of acetic anhydride and 253 g of trietylorthoformate, followed by the addition of 19.2 g of aluminum chloride at room temperature without cooling. The solution was heated to 115° C. for 2 days, then 155 mL of low boiling material was distilled off at 133–145° C. at atmospheric pressure. After cooling to r.t. an additional 75 mL of acetic anhydride and 61.5 g of triethylorthoformate was added and the mixture was heated for an additional 24 hours to 150–155° C. The mixture was cooled to room temperature and poured into 300 mL of a saturated sodium carbonate solution, followed by extraction with 3 times 250 mL of dichloromethane. The organic layer was dried over magnesium sulfate, filtered and concentrated to dryness to give a dark oil, which was distilled at 0.05 mm Hg, Fraction #1, gave 65 g of a clear liquid, b.p. at 40–48° C., TLC, (toluene/5% ethanol): showed unreacted starting material. Fraction #1 can be recycled in follow-up batches. Fraction #2 gave 97 g of a yellow oil, b.p. at 130 to 145° C. Addition of petroleum ether gave 5. m.p.: 53–56° C., NMR (CDCl$_3$), ppm: 1.34 (t,3H); 6.3 (s,3H); 4.1 (q,2H).

No yield was calculated because Fraction #2 is a mixture of (5) and (6).

EXAMPLE 3

Synthesis of 2-amino-4-metbylpyridine-3-carbonitrile (7)

A mixture of (5) and (6) (97 g) obtained from the previous experiment (Fraction #2) was added to 1 L of ethanol. Anhydrous ammonia was passed though the solution without cooling, using a fritted filter candle. After 15 minutes, the mixture was heated to reflux for two hours, then poured into 2 L of water. The product was extracted with three times 300 mL of methylene chloride. The organic phase was dried over MgSO$_4$, filtered and concentrated to dryness. Addition of ether gave 49 g (39.0%) of (7) calculated for 100 g of Isopropylidenemalononitrile (4) (taking into consideration recovered material). m.p.: 148–151° C., NMR (CDCl$_3$), ppm: 2,4 (s,3H); 5.4 (bs,2H); 6.57 (d,1H); 8.07 (d,1H).

EXAMPLE 4

Synthesis of 2-hydroxy-4-methylpyridine-3-carbonitrile (8)

To a 2 L three neck flask equipped with a stirrer, thermometer and dropping funnel was added 750 mL of water and 20 mL of sulfuric acid. To the solution was added 26.6 g of (7). The suspension was warmed to approximately 50° C. until everything dissolved. The solution was cooled in an ice bath to 10° C. then a solution of 20.7 g of sodium nitrite in 100 mL of water was dropped in slowly over a period of 5 hours, maintaining the temperature below +15° C. After the addition, the reaction mixture was stirred at ambient temperature overnight. The yellow crystalline material was filtered, dried under vacuum to give 12.8 g (47.8%) of (8). m.p.: 238–240° C., NMR (DMSO); ppm: 2.4 (s,3H); 3.5 (bs,1H); 6.26 (m,1H); 9.68 (m,1H).

Anal. Calcd.: C, 62.68; H, 4.51; N, 20.88% Found: C, 62.75; H, 4.79; N, 20.95% MS: (EI) m/z 134, 105

EXAMPLE 9

Synthesis of 2-chloro-4-methylpyridine-3-carbonitrile (9)

To a 250 mL flask equipped with a magnetic stirrer was added 10 g of 2-hydroxy-4-methyl-3-pyridinylcarbonitrile (8) and 60 mL of phosphorous oxychloride. The mixture was refluxed for one hour. The excess POCl$_3$ was distilled under reduced pressure. The residue was poured into water. The crystalline material was filtered and dried at to give 10.2 g (89.2%) of (9). m.p.: 109–110° C., NMR (DMSO); ppm: 2.56 (s,3H); 7.6 (bs,1H); 8.56 (m,1H).

MS: (EI) m/z M$^+$ 152,146

EXAMPLE 10

Synthesis of 2-chloro-4-methylpyridine-3-carboxamide (10)

A solution of 6.33 g of 2-chloro-4-methyl-3-pyridine carbonitrile (9) in 6 mL concentrated H$_2$SO$_4$ was stirred at 100° C. for one hour, added ice water, made alkaline with ammonium hydroxide and extracted with ethyl acetate. The extract was dried and the solvent removed to leave a crystalline residue. Recrystallization from ethyl acetate gave 4.9 g (69%) of (10).

m.p.: 178–180° C., NMR (DMSO); ppm: 2.3 (s,3H); 7.3 (m,1H); 7.75, 8.80 (NH$_2$); 8.2 (m,1H).

Anal Calcd.: C, 49.28; H, 4.14; Cl, 20.78, N, 16.42% Found: C, 49.43; H, 4.23; Cl, 20.65; N, 16.52% MS: (EI) m/z 170, 154, 126

EXAMPLE 11

Synthesis of 3-amino-2-chloro-4-methylplridine (1)

A solution of 11.7 g (0.293 mole) of sodium hydroxide in 11 mL of water was stirred and cooled to 0° C. Bromine 14.2 g (0.293 mole) was added dropwise maintaining the temperature at ≈0° C. To a pale yellow solution was added 13.2 g (0.077 mole) of 2-Chloro-4-methylnicotinamide (10) in portions at 0–5° C. The ice-bath was removed and the reaction mixture warmed to 75° C. over one hour and maintained at 60–75° C. for an additional 2 hours. The mixture was cooled overnight and the crystalline product collected by filtration to give 10 g (90.6%) of the title compound [mp: 62–64° C.]. NMR and MS was identical to data reported by Hargrave, et al., *J. Heterocyclic Chem.*, 34, 223 (1991).

What is claimed is:

1. A method for making 3-amino-2-chloro-4-methylpyridine comprising the following steps:

(a) reacting malononitrile with acetone to yield isopropylidenemalononitrile;

(b) condensing the isopropylidenemalononitrile so produced with triethyl orthoformate in acetic acid anhydride yield a mixture of 2-(3-ethoxy-1-methyl-(E)-2-propenylidene)malononitrile and 2-(3,3-diethoxy-1-methylpropylidene)malononitrile;

(c) treating the mixture of 2-(3-ethoxy-1-methyl-(E)-2-propenylidene)malononitrile and 2-(3,3-diethoxy-1-methylpropylidene)malononitrile so produced with anhydrous ammonia in ethanol, to effect ring closure, thus producing 2-amino-4-methyl-pyridine-carbonitrile;

(d) reacting the 2-amino-4-methyl-pyridine-carbonitrile so produced with sodium nitrite, to yield the diazonium salt thereof, and thereafter treating the diazonium salt in situ with water to yield 2-hydroxy-4-methyl-3-cyanopyridine;

(e) reacting the 2-hydroxy-4-methyl-3-cyanopyridine so produced with phosphorus oxychloride to yield 2-chloro-4-methyl-3-pyridinecarbonitrile;

(f) treating the 2-chloro-4-methyl-3-pyridinecarbonitrile so produced with concentrated sulfuric acid, to effect hydrolysis, to yield 2-chloro-4-methyl-3-carboxamide; and, (g) converting the 2-chloro-4-methyl-3-carboxamide so produced, via the Hofmann reaction (treatment with solution of chlorine or bromine in excess sodium hydroxide), to 3-amino-2-chloro-4-methylpyridine.

* * * * *